United States Patent [19] [11] 4,260,562
Linhart et al. [45] Apr. 7, 1981

[54] PREPARATION OF O,N-DISUBSTITUTED HYDROXYLAMINES

[75] Inventors: Friedrich Linhart, Heidelberg; Bjoern Girgensohn, Mannheim; Gernot Reissenweber; Eckhard Hickmann, both of Ludwigshafen, all of Fed. Rep. of Germany

[73] Assignee: BASF Aktiengesellschaft, Fed. Rep. of Germany

[21] Appl. No.: 124,964

[22] Filed: Feb. 27, 1980

[30] Foreign Application Priority Data

Mar. 22, 1979 [DE] Fed. Rep. of Germany ...... 2911246

[51] Int. Cl.³ .................. C07C 85/00; C07C 85/20; C07C 85/24
[52] U.S. Cl. .................................................. 564/300
[58] Field of Search ........ 260/563 R, 563 C, 583 DD

[56] References Cited

U.S. PATENT DOCUMENTS

| | | | |
|---|---|---|---|
| 3,112,345 | 11/1963 | Stansbury et al. | 260/563 C |
| 3,157,702 | 11/1964 | Flack et al. | 260/563 C X |
| 3,207,787 | 9/1965 | Levy | 260/563 R |
| 3,993,772 | 11/1976 | Pommer et al. | 424/285 |

FOREIGN PATENT DOCUMENTS

| | | | |
|---|---|---|---|
| 1931927 | 1/1970 | Fed. Rep. of Germany | 260/563 R |
| 2455082 | 8/1976 | Fed. Rep. of Germany | 260/563 R |
| 46-15089 | 4/1971 | Japan | 260/563 C |
| 50-49209 | 5/1975 | Japan | 260/563 R |

OTHER PUBLICATIONS

Adams et al, "J.A.C.S.", vol. 45, pp. 2175-2178 (1923).
Houben-Weyl, "Methoden der Organischen Chemie", Teil 2, pp. 137-151 (1955).
Taylor et al., "J. Org. Chem.", vol. 41, pp. 1135-1140 (1976).
Bourguel, "Bull. Soc. Chim. France", vol. 43, pp. 231-237 (1928).
Jones et al., "J.A.C.S.", vol. 52, pp. 669-679 (1930).
Houben-Weyl, "Methoden der Organischen Chemie", vol. 11/1, p. 495 (1957).

*Primary Examiner*—John Doll
*Attorney, Agent, or Firm*—Keil & Witherspoon

[57] ABSTRACT

O,N-Disubstituted hydroxylamines are prepared by reacting O-substituted ketoximes with hydrogen in the presence of a platinum catalyst at from 35 to 50 bar, in a medium containing a mineral acid.

The O,N-disubstituted hydroxylamines I obtained by the process of the invention are valuable starting materials for the preparation of dyes, crop protection agents and drugs.

9 Claims, No Drawings

PREPARATION OF O,N-DISUBSTITUTED HYDROXYLAMINES

The present invention relates to a process for the preparation of O,N-disubstituted hydroxylamines by reacting O-substituted ketoximes with hydrogen in the presence of a platinum catalyst at from 35 to 500 bar in a medium containing a mineral acid.

O-Methyl-N-cyclohexylhydroxylamine can be prepared in the form of its salt by a multi-stage process from ethyl chloroformate and cyclohexylhydroxylamine, the process proceeding via the N-hydroxy compound and N-methoxy compound of ethyl N-cyclohexylcarbamte (J. Org. Chem., 41 (1976), 1,135–1,140). This method is expensiive and involved, requires large amounts of solvents and auxiliaries, entails numerous purification operations and working-up operations in the various steps, and gives poor yields and a large number of by-products which pollute the environment.

It is known that hydroxylamines which are unsubstituted at the oxygen atom can be obtained by hydrogenating ketoximes under atmospheric pressure over platinum catalysts in the presence of hydrochloric acid in an aqueous alcoholic medium (Bull. Soc. Chim. France, 43 (1928), 231–237). However, this method is only suitable for the preparation of O-unsubstituted hydroxylamines. Further, it is known that O-alkylketoximes can similary be reduced to O,N-dialkylhydroxylamines under a hydrogen pressure of from 1 to 3 bar (J. Amer. Chem. Soc., 52 (1930), 669–679), but even after very long reaction times of up to 44 hours only unsatisfactory yields are achieved. O-Alkyl-N-cycloalkylhydroxylamines have not been prepared by this process.

We have found that an O,N-disubstituted hydroxylamine of the formula

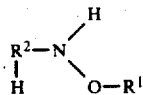

where $R^1$ is an aliphatic radical and $R^2$ is a cycloaliphatic radical which may or may not be substituted by aliphatic radicals, is obtained in an advantageous manner by reacting a ketoxime with hydrogen under pressure in the presence of a platinum catalyst and of a mineral acid, if an O-substituted ketoxime of the formula

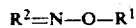

where $R^1$ and $R^2$ have the above meanings, is reacted with excess hydrogen under a pressure of from 35 to 500 bar.

Where O-methylcyclohexanone-oxime is used, the reaction may be represented by the following equation:

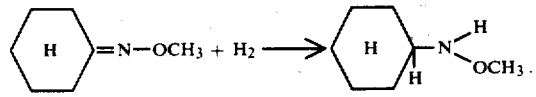

Compared to the conventional process, the process according to the invention gives O,N-disubstituted hydroxylamines more simply and more economically, and in better yield and greater purity. The rate of reaction is higher and the life of the catalyst, especially at the higher pressures within the range according to the invention, is relatively longer. All these advantageous results are surprising in view of the prior art, since it is known from Houben-Weyl, Methoden der Organischen Chemie, Georg Thieme Verlag, Stuttgart 1957, Volume 11/1, page 495, that oximes are very easily reduced to amines via the hydroxylamine stage. For this reason, only the stoichiometric amount of hydrogen for the amount of oxime employed is as a rule used in the conventional processes. Hence it was to be expected that in the process according to the invention, in which excess hydrogen and high pressures are used, amines would be obtained as end products. It was also to be expected that catalyst poisoning, which reduces the life of the catalyst, would occur substantially more rapidly at a higher hydrogen pressure and with the catalyst subjected to more severe conditions.

Preferred starting materials II and accordingly preferred end products I are those where $R^1$ is alkyl of 1 to 7 carbon atoms and $R^2$ is cycloalkylene of 5 to 8 carbon atoms, which may be substituted by 3, 2 or especially 1 alkyl, each of 1 to 7 carbon atoms, or may, in particular, be unsubstituted. The above radicals may in addition be substituted by groups which are inert under the reaction conditions, for example alkyl of 1 to 4 carbon atoms.

Examples of suitable starting materials II are O-methyl-, O-ethyl-, O-propyl-, O-isopropyl-, O-butyl-, O-sec.-butyl-, O-isobutyl-, O-tert.-butyl-, O-pentyl-, O-hexyl-, O-heptyl-, O-octyl-, O-nonyl- and O-decylcyclohexanone-oxime; corresponding oxygen-substituted cyclopentanone-oximes, cyclohepentanone-oximes and cyclooctanone-oximes; corresponding oxygen-substituted cyclohexanone-oximes which in addition are monosubstituted in the 2-, 3- or 4-position of the cycloalkyl ring by methyl, ethyl, propyl, isopropyl, butyl, sec.-butyl, tert.-butyl or iso-butyl, or are disubstituted by such groups in the 2,3-position, 2,4-position, 2,5-position, 2,6-position, 3,4-position or 3,5-position or are trisubstituted by such groups in the 2,3,4-, 2,3,5-, 2,3,6-, 3,4,5-, 2,4,6- or 3,4,6-position, the substituents, in the case of disubstitution or trisubstitution, being identical or different; and corresponding cyclopentanone-oximes, cycloheptanone-oximes and cyclooctanone-oximes substituted at the oxygen atom and in the cycloalkyl ring.

The reaction is in general carried out continuously or batchwise at from $-70°$ to $+100°$ C., preferably from $-50$ to $+50°$ C., especially from $-20°$ to $+30°$ C., under a pressure of from 35 to 500 bar, preferably from 40 to 300 bar, especially from 40 to 150 bar. The reaction takes place with very good yield even at a pressure of as little as 40 bar, but the life of the catalyst is less than when using a hydrogen pressure of 120 bar. The pressure may be the autogenous pressure of the reaction mixture, especially of the excess hydrogen, but may be boosted by introducing an inert gas, for example nitrogen. Advantageously, a solvent which is inert under the reaction conditions is used. Examples of suitable solvents are alkanols and cycloalkanols, eg. ethanol, methanol, n-butanol, isobutanol, tert.-butanol, glycol, n-propanol, isopropanol, amyl alcohol, cyclohexanol, 2-methyl-pentan-4-ol, ethylene glycol monoethyl ether, 2-ethylhexanol and methylglycol, amongst which alkanols of 1 to 4 carbon atoms, especially methanol and ethanol, are preferred, and mixtures of the above with one another and/or with water. Advantageously, the solvent is used in an amount of from 100 to 10,000 percent by weight, preferably from 400 to 2,000 percent by weight, based on starting material II.

The reaction is carried out in the presence of an acid, advantageously in an amount of from 1 to 10, especially from 1 to 5, equivalents per mole of starting material II. Examples of suitable acids are hydrogen chloride, hydrogen bromide, hydrogen iodide, sulfuric acid and phosphoric acid. Amongst aqueous acids, those of from 5 to 98 percent strength by weight, for example hydrochloric acid of from 20 to 38 percent by weight or sulfuric acid of from 20 to 98 percent strength by weight, are advantageous. Hydrochloric acid and sulfuric acid are preferred acids.

The reaction is carried out in the presence of platinum and/or of a platinum compound, in general using from 0.1 to 10 percent by weight, preferably from 0.5 to 5 percent by weight, based on starting material II, of platinum in the form of the metal and/or in the form of one of its compounds, in particular a finely divided compound. Where the metal is used, it may be in a finely divided form or in a shaped form, for example ribbon or gauze. Other specific examples of suitable catalysts are platinum black, platinum sponge, platinum powder, platinum oxide, platinum bromide, platinum arsenide, platinum chloride, platinum nitrate, platinum iodide, platinum oxide, platinum sulfide, platinum sulfate and complex salts, eg. tetrachloroplatinates, tetraamineplatinum chlorides, diamine-platinum chlorides and hexachloroplatinates. Alloys of platinum with other metals, for example rhodium, advantageously in a proportion of from 0 to 15 percent by weight of metal, based on the alloy, may also be used.

The said catalysts may also advantageously be supported in a conventional manner on carriers, for example active charcoal, barium sulfate, graphite, pumice, asbestos, silica gel, alumina, aluminosilicates or zeolites, such supported catalysts then being used for the hydrogenation. The platinum oxide used is in particular $PtO_2.H_2O$ prepared by Adams' method (J. Amer. Chem. Soc. 45 (1923), 2,175–2,178). Such supported catalysts may be prepared in any desired manner, for example by impregnating the carrier with an appropriate solution of the platinum salt, or by kneading or mixing the components and milling the mixture. Details of the preparation of catalysts, especially supported catalysts, may be found in Houben-Weyl, Methoden der Organischen Chemie, Volume 4/2, pages 137 et seq. The reaction is carried out with an excess of hydrogen, advantageously with from 5 to 10,000, preferably from 50 to 1,000, moles per mole of starting material II. The hydrogen may be fed to the reaction mixture continuously or stepwise, and/or the catalyst itself may be recharged with hydrogen after a certain reaction time.

The reaction may be carried out as follows: a mixture of starting material II, acid, hydrogen, hydrogenation catalyst and solvent is kept for from 1 to 6 hours at the reaction temperature and reaction pressure. The end product is then isolated from the reaction mixture in a conventional manner, for example by filtering, evaporating the filtrate, dissolving the residue in water and extracting the aqueous mixture.

The O,N-disubstituted hydroxylamines I obtainable by the process of the invention are valuable starting materials for the preparation of dyes, crop protection agents and drugs. For example, the N-methoxy-N-cycloalkyl-2-methyl-3-furancarboxamides described in U.S. Pat. No. 3,993,772 and the O-methyl-N-cyclohexyl-2,5-dimethylfuran-3-hydroxamic acid described in German Pat. No. 2,455,082 may be prepared by reacting the O,N-disubstituted hydroxylamines with diketene and subsequently with α-hydroxyaldehydes or α-hydroxyketones. The compounds referred to in the two patents cited are, as explained there, valuable fungicides by virtue of their action against phytopathogenic fungi, and are used as crop protection agents, seed dressings and wood preservatives.

In the Examples which follow, parts are by weight.

EXAMPLE 1

O-Methyl-N-cyclohexylhydroxylamine (a) Reaction: 124.5 parts of O-methylcyclohexanone-oxime, 800 parts of ethanol, 116 parts of 85 percent strength sulfuric acid and 1 part of a platinum/active charcoal catalyst (containing 10% by weight of Pt, based on charcoal) are treated, in a pressure vessel, at 20° C., with hydrogen under a pressure of 40 bar, whilst mixing thoroughly. A total of 10 parts of hydrogen is used. After 4 hours no further hydrogen is absorbed; 2.1 parts of hydrogen have been consumed. After letting down the pressure, the catalyst is filtered off, the filtrate is evaporated, the residue is dissolved in water, the solution is extracted with cyclohexane, the extract is rendered alkaline with ammonia, the oil which has precipitated is taken up in methylene chloride, the solution is dried and concentrated, and the residue is distilled. 110 parts of O-methyl-cyclohexylhydroxylamine (87% of theory) of boiling point 65° C./25 mbar are obtained.

(b) Comparative experiment: 127 parts of O-methyl-cyclohexanone-oxime, 800 parts of ethanol, 100 parts of 37 percent strength by weight hydrochloric acid and 1.3 parts of a platinum/active charcoal catalyst (containing 10% by weight of platinum, based on charcoal) are initially introduced into a stirred vessel. Hydrogen under a pressure of 1.5 bar is then introduced, with thorough stirring. A total of 5 parts of hydrogen is used. After 22 hours at 20° C. and 1.5 bar, 2 parts of hydrogen have been consumed. The filtrate is evaporated, the residue is dissolved in water and the solution is rendered alkaline by adding ammonia. No O-methyl-N-cyclohexylhydroxylamine is obtained.

EXAMPLE 2

500 parts of ethanol, 147 parts of 98 percent strength by weight sulfuric acid, 27 parts of water, 155 parts of O-isopropylcyclohexanone-oxime and 1 part of a platinum/active charcoal catalyst (containing 10% by weight of Pt, based on charcoal) are treated, in a pressure vessel, at 20° C., with hydrogen under a pressure of 40 bar for 3 hours, with thorough mixing. A total of 20 parts of hydrogen is used. 2.1 parts of hydrogen are consumed. The catalyst is then filtered off and the filtrate is evaporated. The residue is dissolved in water, the solution is extracted with cyclohexane, the extract is rendered alkaline with sodium carbonate and the oil which separates out is dried and distilled. 139 parts of O-isopropyl-N-cyclohexylhydroxylamine (89% of theory), of boiling point 86° C./20 mbar, are obtained.

EXAMPLE 3

258 parts of O-methylcyclohexanone-oxime, 800 parts of ethanol, 196 parts of 98 percent strength by weight sulfuric acid and 2.5 parts of a platinum/active charcoal catalyst (containing 5% by weight of Pt, based on charcoal) are introduced into a pressure vessel and hydrogenated at 20° C. under a hydrogen pressure of 120 bar, with vigorous stirring, until the pressure remains constant. A total of 50 parts of hydrogen is used. 4.1 parts of hydrogen are consumed. After working up similarly to Example 1a), 230 parts of O-methyl-N-cyclohexylhydroxylamine (89% of theory) are obtained.

Using the same catalyst and also otherwise identical conditions, the following yields are achieved in ten successive hydrogenations: 84%; 82%; 85.5%; 84%; 86%; 85%; 82%; 84%; 86%; 85%.

EXAMPLE 4

127 parts of O-methylcyclohexanone-oxime, 500 parts of ethanol, 100 parts of 37 percent strength by weight aqueous hydrochloric acid and 1.25 parts of a platinum/active charcoal catalyst (containing 5% by weight of Pt, based on charcoal) are mixed in a pressure vessel. The mixture is then hydrogenated for 4 hours at 20° C. under 70 bar hydrogen pressure. A total of 30 parts of hydrogen is used. 2.2 parts of hydrogen are consumed. The catalyst is then filtered off, most of the solvent is evaporated off and the residue is taken up in water. The aqueous solution is rendered alkaline by adding ammonia and the oil which has precipitated is separated off and distilled, giving 115 parts of O-methyl-N-cyclohexylhydroxylamine (90% of theory) of boiling point 50° C./14 mbar.

We claim:

1. A process for the preparation of an O,N-disubstituted hydroxylamine of the formula

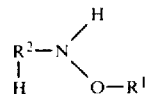

where $R^1$ is an aliphatic radical and $R^2$ is a cycloaliphatic radical which may or may not be substituted by aliphatic radicals, by reacting a ketoxime with hydrogen under pressure in the presence of a platinum catalyst and of a mineral acid, wherein an O-substituted ketoxime of the formula

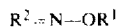

where $R^1$ and $R^2$ have the above meanings, is reacted with excess hydrogen under a pressure of from 35 to 500 bar.

2. A process as claimed in claim 1, wherein the reaction is carried out at from $-70°$ to $+100°$ C.

3. A process as claimed in claim 1, wherein the reaction is carried out at from $-50°$ to $+50°$ C.

4. A process as claimed in claim 1, wherein the reaction is carried out under a pressure of from 40 to 300 bar.

5. A process as claimed in claim 1, wherein the reaction is carried out in the presence of from 100 to 10,000 percent by weight, based on starting material II, of a solvent which is inert under the reaction conditions.

6. A process as claimed in claim 1, wherein the reaction is carried out in the presence of from 1 to 10 equivalents of an acid per mole of starting material II.

7. A process as claimed in claim 1, wherein the reaction is carried out in the presence of from 0.1 to 10 percent by weight of platinum in the form of the metal and/or of its compounds.

8. A process as claimed in claim 1, wherein the reaction is carried out with a supported catalyst.

9. A process as claimed in claim 1, wherein the reaction is carried out with from 5 to 10,000 moles of hydrogen per mole of starting material II.

* * * * *